United States Patent [19]
Nayak et al.

[11] Patent Number: 6,120,779
[45] Date of Patent: Sep. 19, 2000

[54] USE OF PARTIAL AND COMPLETE SALTS OF CHOLINE AND CARBOXYLIC ACIDS FOR THE TREATMENT OF SKIN DISORDERS

[75] Inventors: Smita Nayak; Vinayak Nayak, both of Marlton, N.J.

[73] Assignee: Soma Technologies, Morganville, N.J.

[21] Appl. No.: 09/015,239

[22] Filed: Jan. 29, 1998

[51] Int. Cl.[7] .............................. A61K 6/00; A61K 7/00; A61K 7/04; A61K 7/025

[52] U.S. Cl. .............................. 424/401; 424/64; 424/61; 424/70.1

[58] Field of Search .............................. 424/401, 61, 64, 424/70.1, 47, 73; 514/844, 847; 564/293

[56] References Cited

U.S. PATENT DOCUMENTS

| | | | |
|---|---|---|---|
| 4,892,737 | 1/1990 | Bodor et al. | 424/449 |
| 5,179,097 | 1/1993 | Angres | 514/255 |

Primary Examiner—Thurman K. Page
Assistant Examiner—S. Howard

[57] ABSTRACT

Novel skin care, hair care, nail care, lip care and related external formulations based on partial and complete choline salts of mono, di, tri and polyvalent carboxylic acids of food, cosmetic and pharmaceutical acids are described. These salts have better moisturizing and treating properties compared to the original acids. They tend to form highly elegant cosmetic treatment products when incorporated into lotions, creams, gels, liquids, bars, sticks, sprays and foam products. The mono choline salts of di and polyvalent carboxylic acids are also described in the invention. These mono choline salts tend to retain or enhance the biological properties of the parent molecule with enhanced solubility and bio-availability. These mono choline salts can be formulated as simple solutions and lotions eliminating need of complicated solubilizing systems. The partial and mono choline salts tend to reduce irritation, burning and stinging sensation common to these carboxylic acids.

15 Claims, No Drawings

USE OF PARTIAL AND COMPLETE SALTS OF CHOLINE AND CARBOXYLIC ACIDS FOR THE TREATMENT OF SKIN DISORDERS

BACKGROUND OF THE INVENTION

1. Field of Invention

This invention relates to dermatological and cosmetic compositions containing partial and complete choline salts of mono, di and poly carboxylic acids containing multifunctional chemical groups for the treatment of a variety of disorders, such as dry irritated skin, acne, lack of skin elasticity, low level of skin moisture, excessive premature skin aging related to environmental factors and skin wrinkling due to aging and issues related to hair. The said ingredients can be administered as alcoholic, aqueous or glycolic toning solutions, low and high viscosity lotions, creams, ointments, sticks, aerosols, foams, shaving creams and lotions, color cosmetics and moistened fabric pads.

2. Description of Related Art

The current invention relates to incorporation of partial and complete choline salts of carboxylic acids in dermatological and cosmetic formulations for the treatment of skin disorders. Such acids are aromatic and aliphatic carboxylic acids or compounds capable of forming salts with weak organic bases by the virtue of keto-enol tautomerism. Several carboxylic acids have been employed in the cosmetic and pharmaceutical industry for the treatment of skin disorders. These compounds are irritating in nature due to their highly acidic nature and hence, their utility is restricted to low concentrations. Organic acids of higher molecular weight are not very active and their use is also limited by their low water solubility. Several alpha hydroxy acids (AHA) utilized in the cosmetic industry suffer from similar problems. The inorganic salts of these AHAs also tend to be irritating and their overall utility is restricted by the irritating, stinging and burning sensation on the naked skin. Complete neutralization of the acidic carboxylic group by inorganic bases also renders these compounds inactive.

U.S. Pat. No. 5,571,518 describes Tricholine citrate as an ester of citric acid with three choline molecules for the treatment of wrinkled and aged skin. This patent emphasizes utility of this ester in a variety of cosmetic compositions for the treatment of said disorders. U.S. Pat. No. 5,425,938 describes cosmetic compositions based on multi-amine functionalized polymer salt of alpha hydroxy acids, alpha ketoacids and related compounds. Treatment of skin keratosis with alpha hydroxy acids and related compounds is described in U.S. Pat. No. 4,234,599. Dicarboxylic acids of 7 to 13 carbon atoms in different dermatological preparations are described by Carl R. Thornfeldt for the treatment of ichthyosis and wrinkling in U.S. Pat. No. 4,885,282. Marcella Nazzaro-Porro in U.S. Pat. No. 4,386,104 describes the use of dicarboxylic acids containing 7 to 13 carbon atoms and their mercapto derivatives for the treatment of acne and skin hyperpigmentation. Specific choline salts of carboxylic acids are not described in literature for the treatment of skin disorders.

SUMMARY OF THE INVENTION

The present invention addresses the need of soluble salts of carboxylic acids capable of delivering the active form of carboxylic acid in a non-irritating form in a cosmetically elegant dosage form. Choline is an essential nutrient in the biosynthetic pathway for normal viable cells. Choline deficiency results in reduced lipoprotein biosynthesis, increased triglycerides and decreased membrane turnover. Choline in the form of phospholipids has been widely used in cosmetic compositions for wound healing, treatment of dry skin, improvement of transepidennal water loss, skin moisturization and anti-inflammatory effects. But its use as a salt of a carboxylic acid is restricted to anti-inflammatory analgesic composition as described in U.S. Pat. No. 4,275,059. By converting the known carboxylic acids in part or as a complete salt of choline, the utilization of the choline can be improved and made widely available to the desired target tissue. The mono carboxylic acid of food, cosmetic and pharmaceutical interest can be converted to the partial salts of choline by neutralization of the said acid with basic choline base or choline bicarbonate. The partial neutralization of the carboxylic acids is of interest as this renders the final composition odor free from amine type odor common to the choline salts. The partial neutralization can be done by adjusting the pH of the final preparation with choline base or choline bicarbonate. For example, a 0.1 to 20% lotion of an alpha hydroxy acid can be adjusted to pH 4.0 with free choline base or choline bicarbonate to get a formulation with high choline content and an appropriate pH for the normal biological activity associated with such products. Such partially neutralized alpha hydroxy acid formulations are completely free from irritation and found to have excellent consumer expectance. The partially neutralized AHA formulations are free from fishy odors in their containers and also on application to the skin.

The pure salts of choline can be made by the reaction of the carboxylic acids with choline in an anhydrous medium. The resulting product can be dried to remove water or recrystallized to get pure salts. Another possible method is to treat the sodium salt of the carboxylic acid with choline chloride in an anhydrous medium and removing the precipitated sodium chloride by filtration. Such methods are required only when a pure salt is required for identification or characterization. For making the cosmetic and drug formulation containing partial and complete salts, the method of in-situ neutralization appears to be convenient and economical. The pure choline salts tend to be hygroscopic and discolor on storage. These exposure-related problems are circumvented by the in-situ neutralization of the carboxylic acids with choline base or choline bicarbonates. The partial salts of alpha hydroxy acids can be mixtures of different alpha hydroxy acids, alpha keto acids, carboxylic acids and beta hydroxy acids. For example, one can formulate a toner containing a mixture of lactic and salicylic acids neutralized to a specific pH with basic choline. Such formulations are devoid of solubility problems normally associated with the aromatic carboxylic acids.

The important aspect of this invention is the partial neutralization of specific carboxylic groups in compounds containing multiple carboxylic acid groups. For example the dicarboxylic acids of 3–32 carbon atoms can be reacted with one mole of choline base or the bicarbonate to get mono choline salts with unique solubility and biological properties. Mono choline salts tend to have increased water and alcohol solubility compared to the free acids. This increased solubility tends to make the formulation more effective, and at the same time, impart properties uncommon to the original acid. Most of the mono carboxylic acid salts of choline tend to retain high level of moisture and are excellent moisturizers for the cosmetic use. Good examples are mono choline salts of adipic acid and azelaic acids, which tend to retain large amounts of water compared to the free acids. Complete and partial choline salts of beta aromatic carboxylic acids like salicylic acid, are also extremely hygroscopic and have good moisturizing properties. Partial neutralization of these acids also solves the problem of discoloration found in the purified isolated complete salts of choline.

Partial salt formation with mono, di and poly carboxylic acids can be generated in-situ by reacting the free acids with the required amount of choline free base or choline bicarbonate at the time of manufacture of the final formulation. In case of the semi-solid and liquid formulations meant for dermatological preparations, this can be easily achieved during the preparation of water or alcohol/glycolic phase of the emulsion. These partial salts arc useful as moisturizers in skin care preparations. They can also be used as healing agents in combination with phospholipids, vitamin E, allantoin, fatty acids, fatty acid esters, herbal extracts, vegetable oils, animal oils, fats, and petrolatum. The mono choline salts are useful in the treatment of acne and can be formulated as clear liquids in hydro alcoholic or glycolic solutions. For example, azelaic acid mono choline salt can be formulated as a clear stable liquid in alcoholic and glycolic medium in excess of 20% concentration. These clear solutions have distinct advantage as they are free from any other oily substances and are easy to apply. The lack of surfactant and other fatty substances in the formulation also makes these formulations much more effective in the treatment of acne and other skin conditions. Choline formulations can also be delivered to the skin as transparent gels by interaction of the free base or bicarbonate with cross linked polyacrylic acid derivatives like Carbomers of different grades. A clear transparent acidic gel is made by the interaction of 0.5 to 1.0% carbomer dispersions with choline bicarbonate or choline base to a pH of 5.0 to 7.0. Such gels have wide applications in skin and hair care products. For example, the interaction of basic choline salt with a carbomer and PVP of different molecular weights can produce clear hair care gels. Similarly, after-shave gels containing panthenol and vitamin E succinate can be made, by the interaction of the acidic carbomer and a basic choline salt.

High water, glycol and alcohol solubility of theses partial complete salts of carboxylic acids of cosmetic interest makes the hair-care formulations less complicated. The hair care products formulated with choline carboxylic acid salts tend to impart excellent wet and dry combability to the hair strands. The hair treatment consisting of mixed choline salts of alpha hydroxy acids and dicarboxylic acids in hydro alcoholic solutions without any other additives, is found to have good hair moisturizing and hair manageability properties compared to the commercially available expensive multi-ingredient hair care products. In a head to head comparison with commercially available moisturizers, meant for dry skin and containing alpha hydroxy acids (Lubriderm® moisture recovery lotion and 4% Alphahydrox®), a 4% partial choline salt of mixed alpha and beta hydroxy acids is found to be better tolerated and preferred in consumer trials. Irritation potential and stinging on dry and damaged skin was substantially low compared to the other products. Clinically mixed choline salt product performed significantly better than the marketed products in global physician's assessment of dry skin at the end of two weeks.

DESCRIPTION OF THE PREFERRED EMBODIMENTS

Natural carboxylic acids have been used widely in a variety of food, pharmaceutical and cosmetic applications. These natural food acids have found use in cosmetic products as moisturizers and for the treatment of fine wrinkles. But these carboxylic acids tend to be very irritating when applied in high concentrations. This irritation potential can be substantially reduced by formation of partial choline salts of these mono, di and poly carboxylic acids and the hydroxy derivatives. A variety of such acids are found in fruits of different types and can be isolated from other is natural sources or produced synthetically. These acids include, but are not limited to ascorbic, lactic, citric, tartaric, malic, fumaric, succinic, hydroxycitric, glycolic, lactobionic, acetic, gluconic, salicylic, hydroxy benzoic, mandelic and benzoic acid. The use of partial choline salts of these carboxylic acids leads to the reduction in the burning and the stinging reaction in cosmetic formulations. This adverse reaction can be further reduced by incorporation of partial choline salts of the aromatic carboxylic acids like salicylic acid or the hydroxy benzoic acids along with the aliphatic mono, di and poly carboxylic acids. The moisturization capacity of the formulation is also substantially increased by incorporation of these partial salts. For example, the combination of partial choline salts of lactic acid and salicylic acid in cosmetic formulation results in elegant moisturizers with reduced irritation and good efficacy.

The poly methylene dicarboxylic acids with 4 carbon atoms (Succinic acid) to 36 carbon atoms (Hexacontanedioic acid) are found in nature and are potential candidates for the mono and di choline salt formation with a wide variety of solubility and moisture holding capacity for the treatment of dry skin, hair and other keratinized tissues. These dicarboxylic acids with their melting points are listed in the following table:

| DICARBOXYLIC ACID | MELTING POINT |
|---|---|
| Succinic acid (C-4) | 185 |
| Glutaric acid (C-5) | 98 |
| Adipic acid (C-6) | 153 |
| Pimelic acid (C-7) | 105 |
| Suberic acid (C-8) | 140 |
| Azelaic acid (C-9) | 107 |
| Sebacic (C-10) | 133 |
| Undecanedioic acid (C-11) | 111 |
| Dodecanedioic acid (C-12) | 128 |
| Brassylic acid (C-13) | 113 |
| Tetradecanedioic acid (C-14) | 126 |
| Pentadecanedioic acid (C-15) | 114 |
| Hexadecanedioic acid (C-16) | 125 |
| Roccelic acid (C-17) | 118 |
| Octadecanedioic acid (C-18) | 124 |
| Nonadecanedioic acid (C-19) | 119 |
| Eicosanedioic acid (C-20) | 124 |
| Heneicosanedioic acid (C-21) | 123 |
| Docosanedioic acid (C-22) | 126 |
| Tricosanedioic acid (C-23) | 127 |
| Tetracosanedioic acid (C-24) | 123 |
| Hexacosanedioic acid (C-26) | 123 |
| Octacosanodioic acid (C-28) | 123–125 |
| Triacontanedioic acid (C-30) | 123 |
| Dotriacontanedioic acid (C-32) | 123 |
| Tetracontanedioic acid (C-34) | 123 |

Succinic acid, glutaric acid and adipic acid are food acids and are widely used in food and pharmaceutical industry as acidulants. Other dicarboxylic acids have limited use and are used only for specific applications. For example, azelaic acid is an approved drug for the treatment of acne. Mono choline salts of lower chain dicarboxylic acids like C-4 to C-10 are not useful as surfactants but the choline salts of higher chain dicarboxylic acids have detergent properties. The mono and di choline salts have higher solubility in water and ethanol. This enhanced solubility of these mono choline salts helps to formulate elegant cosmetic formulations. Mono choline salts of these dicarboxylic acids are odor-free and can be utilized to formulate cosmetic compositions in acidic environment with extended buffer capacity. The water holding properties of these molecules also help in the formulation of moisturizers with properties linked to alpha and beta hydroxy acids.

EXAMPLE 1

After-shave gel based on choline polyacrylate coplymer

| | |
|---|---|
| Carbopol 937 | 0.5% |
| Dexpanthanol | 0.05% |
| Alcohol SD 40 | 20.0% |
| Choline base or bicarbonate to pH 5.5 | qs |
| Water qs | 100% |

EXAMPLE 2

Clear monocholine azelate solution for the treatment of acne.

| | |
|---|---|
| Azelaic acid | 20.0% |
| Choline bicarbonate 70% solution | 25.08% |
| Propylene glycol | 10.0% |
| Alcohol USP | qs |

EXAMPLE 3

Mixed choline salts of lactic and salicylic acids in toning solutions.

| | |
|---|---|
| Lactic acid NF | 2.0% |
| Salicylic acid | 1.0% |
| Methyl paraben | 0.08% |
| Propyl paraben | 0.04% |
| Choline bicarbonate 70% to pH 4.5 | qs |
| Water purified | 100% |

EXAMPLE 4

Skin moisturizing lotion containing 5% adipic acid as mono choline salt.

| | |
|---|---|
| Isocetyl stearate | 7.0 |
| Isostearyl neopentanoate | 3.0 |
| Dow 556 | 1.0 |
| Dimethicone 350 cs | 1.0 |
| Cyclomethicone | 1.0 |
| Cetyl alcohol | 2.0 |
| Ceracynt 945 | 5.0 |
| Span 80 | 1.0 |
| Vitamin E | 0.25 |
| Xanthan gum | 0.05 |
| Glycerin | 3.0 |
| Disodium EDTA | 0.05 |
| Methyl paraben | 0.1 |
| Propyl paraben | 0.05 |
| Adipic acid | 5.00 |
| Choline bicarbonate 70% | 8.1 |
| Water qs | 62.3 |
| Perfume | 0.1 |

EXAMPLE 5

Choline lactate/Lactic acid lotion for the treatment of dry and aged skin

| | |
|---|---|
| Isocetyl stearate | 8.0 |
| Isocetyl neopentanoate | 2.0 |
| Phenyl trimethicone | 3.5 |
| Cyclomethicone | 1.0 |
| Cetyl alcohol | 2.0 |
| Cerasynt 945 | 5.0 |
| Vitamin E | 0.2 |
| Lactic acid | 4.0 |
| Choline bicarbonate 70% qs to pH 4.2 | |
| Disodium EDTA | 0.02 |
| Methyl paraben | 0.1 |
| Propyl paraben | 0.05 |
| Xanthan gum | 0.05 |
| Glycerin | 3.0 |
| Water purified qs | 100.0 |

EXAMPLE 6

Mono choline azelaic acid pads for the treatment of acne or dry irritated skin

| | |
|---|---|
| Azelaic acid | 10.0 |
| Choline bicarbonate 70% | 12.54 |
| Propylene glycol | 20.0 |
| Water DI | 20.0 |
| Alcohol SD 40 qs | 100.0 |

For every 12×20 cm.

Non-woven fabric pad, use 4.5 to 5 gms of the above solution.

EXAMPLE 7

Cleansing toner with mixed choline carboxylates

| | |
|---|---|
| Salicylic acid | 1.00 |
| Lactic acid | 1.00 |
| Butylene glycol | 3.00 |
| Choline bicarbonate to pH 4.0 | qs |
| Methyl paraben | 0.08 |
| Alcohol SD 40 | 20.0 |
| EDTA disodium | 0.05 |
| Pluronic F 127 | 0.50 |
| Water qs | 100.0 |

EXAMPLE 8

Mixed Fruit acid partial choline salts containing clear liquids as moisturizers.

|  |  |
| --- | --- |
| Ascorbic acid | 1.0 |
| Lactic acid | 1.0 |
| Citric acid | 0.5 |
| Tartaric acid | 0.5 |
| Hydroxy citric acid | 0.5 |
| Malic acid | 0.5 |
| Fumaric acid | 0.5 |
| Succinic acid | 0.5 |
| Gylcolic acid | 0.5 |
| Glycerin | 1.0 |
| Choline bicarbonate to pH 3.8 | qs |
| Alcohol SD 40 | 20.0 |
| Water purified qs | 100 |

EXAMPLE 9

Lip treatment complex with moisturizers and partial choline salt of natural acids

|  |  |
| --- | --- |
| Lactic acid | 1.0 |
| Malic acid | 1.0 |
| Ascorbic acid | 1.0 |
| Choline bicarbonate 70% to pH 4.0 | qs |
| Vitamin E | 1.0 |
| Glycerin | 3.0 |
| Menthol | 0.5 |
| Vanilla flavor | 0.5 |
| Lanolin anhydrous qs | 100 |

EXAMPLE 10

Dry scalp/damaged hair treatment formulation with azelaic acid mono choline salt.

|  |  |
| --- | --- |
| Glycerin | 1.0 |
| PEG 400 | 10.0 |
| Azelaic acid | 20.0 |
| Choline bicarbonate | 25.08 |
| Alcohol SD 40 | 25.0 |
| Water DI qs | 100.0 |

EXAMPLE 11

Azelaic acid mono choline lotion for the treatment of cellulite

|  |  |
| --- | --- |
| Isocetyl stearte | 8.0 |
| Isocetyl neopantanoate | 2.0 |
| Phenyl trimethicone | 2.0 |
| Dimethicone 350 cs | 1.0 |
| Cyclomethicone | 1.0 |
| Cetyl alcohol | 2.0 |
| Cerasynt 945 | 5.0 |
| Steareath 20 | 0.2 |
| Vitamin E | 0.2 |
| Caffeine/Standardized tea extract | 1.0 |
| Azelaic acid | 10.0 |
| Choline bicarbonate 70% | 12.5 |
| Disodium EDTA | 0.02 |
| Methyl paraben | 0.1 |
| Propyl paraben | 0.05 |
| Xanthan gum | 0.1 |

-continued

|  |  |
| --- | --- |
| Glycerin | 3.0 |
| extract of *C. mukul*/E & Z guggulsterone | 0.25 |
| Inositol hexanicotinate | 2.0 |
| Water purified qs | 100.0 |

EXAMPLE 12

Azelaic acid mono cholinate clear liquid for the treatment of cellulite

|  |  |
| --- | --- |
| Azelaic acid | 20.0% |
| Choline bicarbonate 70% solution | 25.08% |
| Propylene glycol | 10.0% |
| Caffeine | 1.0% |
| Alcohol USP qs. | 100.0% |

EXAMPLE 13

Natural vinegar containing ear moisturizers.

|  |  |
| --- | --- |
| Natural grape/apple/rice vinegar qs to get | 2% acetic acid |
| Choline bicarbonate to adjust pH to 3.5 |  |
| Benzyl alcohol | 1.0% |
| Glycerin | 1.0% |
| Water qs to | 100.0% |

EXAMPLE 14

Vaginal moisturizing douche containing natural acid choline salts.

|  |  |
| --- | --- |
| Natural vinegar qs | 1.00 acetic acid |
| Lactic acid | 1.00 |
| Glycerin | 3.00 |
| Choline bicarbonate to pH 3.5 | qs |
| Methyl paraben | 0.08 |
| EDTA disodium | 0.05 |
| Pluronic F 127 | 0.50 |
| Water qs | 100.0 |

EXAMPLE 15

Anti-wrinkle skincare compositions containing anthracene, naphthalene carboxylic acid glycosides.

|  |  |
| --- | --- |
| Mixed sennosides A, B, C & D | 0.1 |
| Choline bicarbonate | 0.0274 |
| Alcohol 95% | 25 |
| Sodium CMC High viscosity | 0.5 |
| Glycerin | 5.0 |
| Water qs | 100 |

EXAMPLE 16

Anti-irritation skincare compositions containing boswellic acid and glycerrhizinic acid.

| | |
|---|---|
| Boswellic acids from gum extract | 2.0 |
| Glycyrrhizinic acid | 1.0 |
| Choline bicarbonate | 1.0 |
| Cetyl alcohol | 4.0 |
| Steareth 20 | 0.5 |
| Xanthan gum | 0.06 |
| Methyl paraben | 0.1 |
| Propyl paraben | 0.05 |
| Water qs | 100.0 |

EXAMPLE 17

Hair spray treatment products for dry and damaged hair

| | |
|---|---|
| Adipic acid | 2.5 |
| Azelaic acid | 2.5 |
| Choline bicarbonate 70% | 7.17 |
| PVP K30 | 1.0 |
| Alcohol SD 40 | 25.0 |
| Water qs to | 100.0 |

EXAMPLE 18

Liposomal hair spray containing mono choline azelate for the treatment of dry/damaged hair and reduction in hair loss.

| | |
|---|---|
| Azelaic acid | 5.0 |
| Choline bicarbonate | 6.25 |
| Vitamin E | 0.25 |
| PVP K30 | 1.0 |
| Lecithin Hydro-alcoholic base qs. | 100.0 |

Lecithin and purified water qs for the production of liposomes and achieve the desired encapsulation based on a proprietary process.

EXAMPLE 19

| Nail moisturizing compositions. | |
|---|---|
| Azelaic acid | 5.0 |
| Lactic acid | 1.0 |
| Salicylic acid | 1.0 |
| Choline bicarbonate qs. to pH 4.0 | |
| Dimethyl isosorbide | 20.0 |
| Hydroxy propyl/ethyl cellulose high viscosity grade | 1.0 |
| Alcohol USP qs. | 100.0 |

Clinical significance and comparison of moisturizing ability of choline salts against the marketed products.

Three subjects with excessive dry and flaky skin below the knees to the foot previously treated with various moisturizers like Lubriderm without any favorable effects were selected for the study. These subjects were instructed not to use any skin treatment product for a week before the current study. The placebo and the lotion containing the partial choline salt of lactic acid and adipic acid (pH 4.2) were applied to the two legs (left and right) in random order two times a day for a week. At the end of 7 days, the skin surface was evaluated for roughness, dryness and flakiness under a magnifying glass by a physician. A marked difference in skin texture and dryness was observed in each of the three subjects on the leg that received choline salts of carboxylic acids. After discontinuation of the therapy, on third day, the skin was observed for global improvements. The skin treated with partial choline salts of carboxylic acids showed significant improvement compared to the placebo.

It is understood that the specific examples described in the invention herein are intended to be representative only. Any deviations including but not limited to those described in the invention may be made in the description of the preferred embodiment without departing from the main principle of the invention.

What is claimed is:

1. A method of alleviating dry and irritated skin by topically applying to the skin, a cosmetic composition comprising complete or partial choline salts of pharmaceutically acceptable carboxylic acids.

2. The method of claim 1, wherein the said choline salt in the cosmetic composition is prepared in situ, by
   A) neutralization of the said carboxylic acid or their combinations with free choline base
   B) neutralization of the said carboxylic acids with basic choline salts
   C) neutralization of the said carboxylic acids to a pH range of 1.0 to 9.0 by the choline or its basic salts
   D) partial neutralization of the single carboxylic group from a multi carboxylic acid to get mono or di choline salts or incorporation of the pure choline salts in different ratios to get the desired concentrations.

3. The method of claim 1, wherein the said carboxylic acid in the composition, is either a single ingredient or a combination selected from the group consisting of alpha hydroxy acids, alpha keto acids, beta hydroxy acids, dicarboxylic acids, mono carboxylic acids, amino acids found in nature, polymeric carboxylic acids, and aromatic acids.

4. The method of claim 1, wherein the composition is formulated in the form of skin moisturizing, antiacne, anti dandruff, anticellulite, nail softening, cleansing, dry-scalp moisturizing/conditioning, ear moisturizing/conditioning, hair-care, lip-treatment, sun-screening lotions, creams, gels or liquids.

5. Skin moisturizing compositions, cleansing compositions and dry-scalp moisturizing and conditioning compositions of claim 4, comprising partial or complete choline salts of nontoxic mono, di, tri, and poly carboxylic acids in 0.001 to 50% of the weight of composition.

6. Lip treatment products, hair care products and ear moisturizers and cleansers of claim 4, wherein partial or complete choline salts of mono, di, tri and poly carboxylic acids are in the range of in 0.001 to 20% of the weight of the composition.

7. Acne treatment products of claim 4 comprising partial or complete choline salts of alpha hydroxy acids, salicylic acid, mandelic acid, C-7 to C-20 dicarboxylic acids or boswalic acid in 0.001 to 50% concentration.

8. Nail softening treatment complexes of claim 4 containing partial and complete choline salts of mono, di, tri and poly carboxylic acids in 0.001 to 70% of the weight of the composition.

9. Method of manufacturing the partial salts as described in claim 2 which results in the formation of odor free, color free and stable choline complexes.

10. The method described in claim 2, wherein substantial reduction in local irritation, inflammation, burning and stinging is attained by formation of partial choline salts compared to the free acid formulations.

11. The cosmetic composition according to claim 1, wherein different combinations of aromatic, aliphatic, alpha and beta hydroxy acids along with C-4 to C-36 dicarboxylic acid mono choline salts are used in a pH range of 2 to 8 for the treatment of sun-damaged skin, wrinkles and age spots.

12. Anti-cellulite compositions of claim 4 containing mixed acid salts of choline in 0.01 to 50% concentration in combination with nicotinic acid, inositol hexanicotinate, caffeine, DHEA, and guggulsterone.

13. Mixed or mono choline salts of long chain carboxylic acids and polymeric carboxylic acids of claim 3 in 0.001 to 50% range used with dual intend as an emulsifier/stabilizer or solubilizer while imparting moisturizing properties to skin care products.

14. Partial neutralization of carboxylic acids of claim 2 with choline base to pH range of 2.0 to 8.0 to have better color stability and alleviate odor problems compared to the completely neutralized carboxylic acid salts.

15. Partially neutralized choline salts of carboxylic acids of claim 2 in 0.005 to 50% concentration in an anhydrous base to be molded in different cosmetic solid or semisolid dosage formulations.

* * * * *